United States Patent
Mattiasson et al.

(10) Patent No.: US 6,933,153 B1
(45) Date of Patent: Aug. 23, 2005

(54) METAL ION SPECIFIC CAPACITY AFFINITY SENSOR

(75) Inventors: Bo Mattiasson, Hjarup (SE); Elisabeth Csoregi, Lund (SE); Ibolya Bontidean, Bistrita (RO); Gillis Johansson, Lund (SE); Christine Berggren, Lund (SE); Nigel Brown, West Midlands (GB); Jonathan Lloyd, Amherst, MA (US); Kenneth Jakeman, West Midlands (GB); Jonathan Hobman, Worcestershaire (GB); Jonathan Wilson, London (GB); Daniel Van Der Leile, Mol (BE); Philippe Corbisier, Mol (BE)

(73) Assignees: Vlaamse Instelling Voor Technologish Onderzoek, Mol (BE); School Biological Sciences at the University of Birmingham, Birmingham (GB)

( * ) Notice: Subject to any disclaimer, the term of this patent is extended or adjusted under 35 U.S.C. 154(b) by 0 days.

(21) Appl. No.: 09/508,775
(22) PCT Filed: Sep. 15, 1998
(86) PCT No.: PCT/SE98/01638
§ 371 (c)(1),
(2), (4) Date: Oct. 25, 2000
(87) PCT Pub. No.: WO99/14597
PCT Pub. Date: Mar. 25, 1999

(30) Foreign Application Priority Data

Sep. 15, 1997 (SE) .............................................. 9703315

(51) Int. Cl.$^7$ ............................................. G01N 33/20
(52) U.S. Cl. .................. 436/73; 422/82.01; 422/82.02; 422/82.03; 422/82.04; 422/82.05; 422/56; 436/80; 436/81; 436/82; 436/83; 436/84; 436/149; 436/150

(58) Field of Search ................... 422/56, 82.01–82.05; 435/69.1, 69.3, 69.7; 436/73, 80–84, 149–151; 530/387.3

(56) References Cited

U.S. PATENT DOCUMENTS

| | | | | |
|---|---|---|---|---|
| 4,964,972 A | * | 10/1990 | Sagiv et al. | 204/418 |
| 5,498,538 A | * | 3/1996 | Kay et al. | 435/69.1 |
| 5,500,351 A | | 3/1996 | Eccles et al. | 435/25 |
| 5,594,115 A | * | 1/1997 | Sharma | 530/413 |
| 5,935,823 A | * | 8/1999 | Fowlkes et al. | 435/69.7 |
| 5,972,656 A | * | 10/1999 | Lopez et al. | 435/69.3 |
| 6,111,079 A | * | 8/2000 | Wylie et al. | 530/387.3 |
| 6,306,584 B1 | * | 10/2001 | Bamdad | 435/6 |
| 6,391,590 B1 | * | 5/2002 | Sano et al. | 435/69.7 |

FOREIGN PATENT DOCUMENTS

EP     260 948 A2   4/1988

OTHER PUBLICATIONS

Schlereth, D. D. et al, Journal of Electroanalytical Chemistry 1997, 431, 285–295.*

(Continued)

Primary Examiner—Arlen Soderquist
(74) Attorney, Agent, or Firm—Seed IP Law Group PLLC (57) ABSTRACT

This invention relates to a metal ion specific capacitance sensor with exceptional sensitivity and wide operating range. It is versatile because different kinds of recognition elements can be immobilized directly in a self-assembling monolayer substantially completely covering the surface of the measuring noble metal electrode. The electrode then becomes selective to those metal ions in the solution that show affinity to the recognition element on the surface. Compared to previously described electrochemical sensors, the sensor according to the present invention shows many orders of magnitude better sensitivity because of the unique measuring principle.

20 Claims, 8 Drawing Sheets

OTHER PUBLICATIONS

Liu, J. et al, Israel Journal of Chemistry 1997, 37, 235–239.*

Mirsky, V. M. et al, Biosensors & Bioelectronics 1997, 12, 977–989.*

Rickert, J. et al, Biosensors & Bioelectronics 1996, 11, 757–768.*

Dong, X.–D. et al, Bioelectrochemistry and Bioenergetics 1997, 42, 63–69.*

Madoz, J. et al, Journal of the American Chemical Society 1997, 119, 1043–1051.*

Shen, H. et al, Journal of Solid State Electrochemistry 1997, 1, 148–154.*

Nakano, K. et al, Transactions of the Materials Research Society of Japan 1994, 15A, 635–638.*

Duan, C. et al, Analytical Chemistry 1994, 66, 1369–1377.*

Steinberg, S. et al, Thin Films 1995, 20, 183–205.*

Duan, C. et al, Mikrochimica Acta 1995, 117, 195–206.*

Mattiason, B. et al, Journal of Applied Biochemistry 1979, 1, 377–384.*

Sabatani, E. et al, Journal of Physical CHemistry 1987, 91, 6663–6669.*

Rubinstein, I. et al, Nature 1988, 332, 426–429.*

Cheng, Q. et Al, Analytical Chemistry 1992, 64, 1998–2000.*

Frantz, B. et al, Biochemistry 1990, 29, 4747–4751.*

Tommey, A. M. et al, FEBS Letters 1991, 292, 48–52.*

Huckle, J. W. et al, Molecular Microbiology 1993, 7, 177–187.*

Berggren, C. et al, Analytical Chemistry 1997, 69, 3651–1657.*

Henke et al., "Self–Assembled Monolayers of Monofunctionalized Cyclodextrins onto Gold: A Mass Spectrometric Characterization and Impedance Analysis of Host–Guest Interaction," *Anal. Chem.* 68:3158–3165, 1996.

Radloff et al., "Stability Improvement of an Optochemical Heavy Metal Ion Sensor by Covalent Receptor Binding," *Chemical Abstracts* 126(8):1343, Abstract No. 112425u, 1997.

Radloff et al., "Stability Improvement of an Optochemical Heavy Metal Ion Sensor by Covalent Receptor Binding," *Sensors and Actuators B 35–36*:207–211, 1996.

Rojas et al., "Supported Monolayers Containing Preformed Binding Sites. Synthesis and Interfacial Binding Properties of a Thiolated β–Cyclodextrin Derivative," *J. Am. Chem. Soc.* 117:336–343, 1995.

Steinberg et al., "Ion–Selective Monolayer Membranes Based upon Self–Assembling Tetradentate Ligand Monolayers on Gold Electrodes. 2. Effect of Applied Potential on Ion Binding," *J. Am. Chem. Soc.* 113:5176–5182, 1991.

* cited by examiner

METAL ION SPECIFIC CAPACITY AFFINITY SENSOR

There is a need to measure trace concentration of heavy metal ions in the environment, in medicine, in food and other products. Heavy metals are toxic elements and it is therefore important to be able to determine them on the trace level. Some heavy metals, e.g. copper and zinc, are essential for the living cells. Various classical methods such as atomic absorption spectroscopy, inductively coupled plasma emission spectrometry and plasma emission mass spectrometry are in wide use. These methods require sophisticated instrumentation and skilled personnel. Therefore, there is a need for easier and cheaper methods. Electrochemical methods for metal ion determination include ion selective electrodes, polarography and other voltammetric electrodes. Biosensors are selective and sensitive analytical devices and several different biosensor configurations have been described in the past for heavy metal detection. Whole cell-based biosensors represent one possible design and these can utilize bacteria, yeasts, fungi, lichens, mosses and water plants as recognition element [Wittman, C.; Riedel, K.; Schmid, R. D. Handb. Biosens. Electron. Noses, 1997 299–332]. Another approach is to use enzymes for the detection. So far the use of apoenzymes has been the most successful and widely used method [Mattiasson, B.; Nilsson, H.; Olsson, B. J. Appl. Biochem., 1 1979 377–384]. However, these sensors are characterized by limited selectivity and fairly low sensitivity.

Protein engineering has opened up the possibility to design and produce new proteins with e.g. higher selectivity than natural ones. The fusion protein GST-SmtA (SEQ.ID.NO. 1) has been developed by protein engineering and it is reported to show a broad selectivity towards various heavy metal ions ($Cu^{2+}$, $Zn^{2+}$, $Cd^{2+}$ and $Hg^{2+}$) [Shi, J.; Lindsay, W. P.; Huckle, J. W.; Morby, A. P.; Robinson, N. J. FEBS, 303, 1992 159–163]. Another fusion protein called MerR (SEQ.ID.NO.2) is engineered to be exclusively selective towards $Hg^{2+}$ [Frantz, B.; O'Hallaran. T. V. Biochemistry, 29, 1990 4747–4751]. A third protein, PbrR (SEQ.ID.NO.3) from the strain Alcaligenes eutrophus CH34 (The strain is deposited BCCM under the accession number LMG P-18077) is selective towards $Pb^{2+}$. A fourth protein, MerP (SEQ.ID.NO.4), is selective towards $Hg^{2+}$. It is believed that a large conformational change is taking place when heavy metal ions bind to these proteins. This invention describes a capacitive sensor which can detect these conformational changes directly.

Self-assembled monolayers of thiols, sulfides and disulfides on gold electrodes have been widely studied and long-chain alkanethiols are known to form insulating well-organized structures on gold substrates [Porter, M. D.; Bright, T. B.; Allara, D. L.; Chidsey, C. E. D. J. Am. Chem. Soc 1987, 109, 3559–3568]. The binding formed between the sulphur atom and gold is very strong and the formed self-assembled monolayers (SAM's) are stable in air, water and organic solvents at room temperature [Bain, C. D.; Troughton, E. B.; Tao, Y.-T.; Evall, J.; Whitesides, G. M.; Nuzzo, R. G. J. Am. Chem. Soc. 1989, 111, 321–335]. It has been suggested that micro-contact printing [Mrksich, M.; Whitesides, G. M. Tibtech 1995, 13, 228–235] and photolithography [Bhatia, S. K.; Hickman, J. J.; Ligler, F. S. J. Am. Chem. Soc. 1992, 114, 4432–4433] can be used to pattern surfaces with functionalized self-assembled monolayers for biosensor production with low cost for a diversity of applications, but until now it has not been possible to produce direct affinity sensors with high sensitivity.

Rojas et al., J. Am. Chem. Soc. 1995, 117, 336–343 relates to a capacity affinity sensor for assaying ferrocene, Per-6-thio-β-cyclodextrin, a compound capable of forming a self-assembling monolayer, is bound to a gold surface. Monolayer defects are covered by treatment with a solution of ferrocene and pentanethiol. Steinberg et al., J. Am. Chem. Soc. 1991, 113, 5176–5182 relates to a capacity affinity sensor which has been produced by adsorbing 2,2'-thiobis (ethylacetoacetate) or by simultaneously adsorbing 2,2'-thiobis (ethylacetoacetate) and n-petadecyl mercaptane to a gold surface. The effect of applied potential ion binding is investigated.

SUMMARY OF THE INVENTION

It has now turned out that unexpectedly good metal ion-specific capacity affinity sensors suitable for determining the presence of a certain heavy metal ion by capacitance measurement, comprising the steps of:

a) providing a piece of a noble metal, where said piece optionally can be a rod, or alternatively a piece of insulating material such as glass, silicon or quartz, on which a noble metal is sputtered or printed;

b) providing a first SAM-forming molecule comprising a coupling group.

c) contacting the piece in step a) with the first SAM-forming molecule in step b), thereby obtaining a self-assembling monolayer on said noble metal surface;

d) contacting said self-assembling monolayer on said noble metal piece with a molecule specifically binding said heavy metal ion, thereby coupling said molecule to the self-assembling monolayer;

e) contacting the piece obtained in step d) with a second SAM-forming molecule, thereby obtaining a noble metal surface that is at least 90%, preferably at least 95%, more preferably at least 97%, and most preferably at least 99% covered with a self-assembling monolayer.

DETAILED DESCRIPTION OF THE INVENTION

The detection limits reported in this invention are several orders of magnitude better than those reported previously for electrochemical metal detection methods. The insights behind this invention are that the recognition layer must be thin, well-ordered and it must cover at least 90%, preferably at least 95%, more preferably at least 97%, and most preferably at least 99% of the sensor surface. In a subsequent step, any free spots between the recognition elements are "plugged", i.e. covered with a second self-assembling monolayer-forming molecule, e.g. an alkanethiol comprising 3–25 carbon atoms preferably in a straight chain, after obtaining a self-assembling monolayer comprising affinity groups, thereby increasing the tightness and insulation. A capacitive biosensor is covered by a self assembling monolayer on which the recognition element is immobilised toward the solution. Electrically it is equivalent to a capacitor between the conducting metal electrode and the conducting solution.

Any part of the surface that allows the aqueous solution to penetrate below the plane where the recognition takes place will act like a short-circuiting element. The capacitance will therefore increase due to the higher dielectric constant of the penetrating aqueous solution. Oxide layers are not well ordered and it is therefore impossible to form a dense recognition layer. Self-assembled monolayers are much better ordered and a more perfect coverage can therefore be expected in the immobilized layers. Furthermore, the self-assembled monolayers are much thinner than the oxide layers, resulting in a larger capacitance in series with the capacitance formed when molecules bind on the surface. This makes it easier to detect changes in the capacitance when an analyte binds to the surface.

This invention describes an affinity sensor for monitoring heavy metal ions at trace levels, optionally based on bioengineered proteins. A specifically heavy metal-binding substance is coupled to a conducting surface via a self-assembling monolayer. The binding of the desired heavy metal ion to said substance causes a conformation change which is associated with a change in capacitance. The grafted recognition layer should be electrically insulating to prevent interferences from redox couples in the electrolyte and high Faradaic background currents. On the other hand, it should be as thin as possible in order to achieve high sensitivity. The use of self-assembled binding to gold or other self-assembling metals gives especially thin and compact layers. The invention also shows how additional insulation can be obtained by plugging with a different type of self-assembling molecule.

Accordingly, the present invention relates to a method for producing a metal ion specific capacity affinity sensor, wherein a piece of a noble metal is covered with a layer of a self-assembling monolayer comprising affinity groups. Subsequently any free spots on the noble metal surface is covered by a second self-assembling monolayer-forming molecule.

In another aspect, the present invention relates to a metal ion specific capacity affinity sensor comprising a noble metal piece substantially completely covered with a self-assembling monolayer comprising affinity groups that specifically binds to a certain molecule of interest.

In yet another aspect, the present invention relates to a method for qualitatively or quantitatively determining the presence of a certain heavy metal ion of interest. A metal ion specific capacity affinity sensor, comprising a noble metal surface substantially completely covered with a self-assembling monolayer comprising affinity groups that specifically binds to a certain heavy metal ion of interest, is contacted with a liquid sample comprising the heavy metal ion of interest and the sensor's capacitance change is determined.

In a further aspect, the present invention relates to using said sensors for analysing certain heavy metal ions of interests, such as $Zn^{2+}$, $Hg^{2+}$, $Cd^{2+}$, $Cu^{2+}$ and $Pb^{2+}$.

Definitions:

As disclosed herein, the terms "self-assembled monolayer" and "SAM" are synonyms and relate to the spontaneous adsorption of film components from a solution onto a solid surface making a well-ordered monolayer. Such a layer on gold substrates have previously been described [Porter, M. D.; Bright, T. B.; Allara, D. L.; Chidsey, C. E. D. *J. Am. Chem. Soc.* 1987, 109, 3559–3568].

As disclosed herein, the term "noble metal" relates to a metal chosen from the group of gold, silver, copper, platinum and palladium. Gold is preferred.

As disclosed herein, the terms "group/molecule specifically binding to a certain heavy metal ion of interest", respectively relate to a group or a molecule which specifically binds to a certain heavy metal ion. Any molecule having such binding characteristics can be used in the present invention. Examples of such molecules are chelating compounds and certain proteins. In a preferred embodiment, the proteins having the sequences according to anyone of SEQ.ID.NO. 1, SEQ.ID.NO.2, SEQ.ID.NO.3 and SEQ.ID.NO.4 are used.

As disclosed herein, the term SAM-forming molecule relates to a molecule having the ability of forming a self-assembling monolayer on a noble metal. A SAM-forming molecule comprises at least one thiol, sulphide or disulphide group. Heavy metal-binding molecules, are, however, not SAM-forming molecules on their own. They must be coupled to small SAM-forming molecules in a separate step. Examples of such small SAM-forming molecules are thioctic acid and cysteamine. This coupling step is carried out after formation of the self-assembling monolayer on the noble metal surface. The skilled person is well aware of how to choose suitable coupling reactions and coupling groups. In the following examples, a self-assembling monolayer consisting of thioctic acid is activated by 1-(3-dimethylaminopropyl)-3-ethyl-carbodiimide. Subsequently a heavy metal-binding molecule is coupled to the activated monolayer. However, other similar coupling reactions are described in the literature.

As disclosed herein, the term "plugging" refers to treatment in a solution containing a thiol, sulphide or disulphide after immobilization of the affinity group either to a self-assembling monolayer on a noble metal surface or, in case the affinity molecule comprises available thiol, sulphide or disulphide groups rendering the affinity molecule to be a SAM-forming molecule per se, directly to the noble metal surface, in order to block any unblocked spots on said surface. As already mentioned, it is necessary that the noble metal surface is as completely covered by a SAM as possible in order to optimize the sensitivity of the sensor.

As disclosed herein, the term "heavy metal ion" relates to metal ions having atomic numbers higher than 21, such as ions of Ti, V, Cr, Mn, Fe, Co, Ni, Cu, Zn, Zr, Nb, Mo, Ru, Rh, Pd, Ag, Cd, In, Sn, Ta, W, Re, Os, Ir, Pt, Au, Hg, Tl, Pb and Bi. The present invention is particularly usefull for determining the presence of $Zn^{2+}$, $Hg^{2+}$, $Cd^{2+}$, $Cu^{2+}$ and $Pb^{2+}$.

As disclosed herein, the term "functional derivatives" relates to derivatives in which the original amino acid sequence has been modified or changed by insertion, addition, substitution or exclusion of one or more amino acids, as well as derivatives containing multiples of the original sequence or parts thereof.

As disclosed herein, SCE stands for the saturated calomel electrode; Potentiostatic perturbation means a fast change in potential. PEGDGE stands for polyethylene-glycol-diglycidyl-ether. BSA means bovine serum albumin.

In this invention a solution containing the heavy metal ions to be determined is allowed to have electrical contact with a conducting surface containing the recognition element after which the capacitance or impedance change is determined The capacitance change takes place between the solution and a metal surface, consisting of solid metal or metal sputtered on an underlaying non-conducting surface. Faradaic reactions with the metal as well as background currents are blocked by the recognition element on the surface, eventually improved by treatment with auxiliary compounds which improve the insulation. The recognition element is bound to the metal surface, either directly through self-assembly, or by binding it to a self-assembled compound on the electrode. It can also be bound through adsorption, polymerization or coating. Measurements are made by applying varying voltages to the electrode using potentiostatic methods and analyzing the current changes. The sensitivity can be improved by allowing a solution containing a secondary specific ligand to bind to the analyte already on the surface, thereby increasing the size of the bound aggregate and the capacitance change.

The invention will now be described in more detail with reference to the enclosed drawings.

If a solid measuring metal electrode is used, a gold rod of typically 3 mm in diameter, is polished, cleaned and coated through self-assembly with a recognition element or with a compound which can be coupled with a recognition element. A great number of coupling methods are known and may be used as suitable alternatives to those described in the examples. It is also possible to use metal sputtered or printed on glass, quarts, silicon or another insulating material as disposable electrodes. After cleaning the electrodes are coated in batch and inserted in a quick-connect measuring cell. A number of different recognition elements can be immobilized on the same sputtered electrode if they are separated by insulating parts and connected to the potentiostat with switches which can be controlled by a microprocessor.

The inverse total capacitance is the sum of the inverse capacitances of each layer in series, i.e. the thioctic acid layer, the protein layer and the capacitance between the double layer space charge and solution. If one of these is small compared to the others, it will dominate the total capacitance. Especially if self-assembled parts give rise to a small capacitance, it will dominate over the capacitances in the recognition layer. Changes in the recognition layer will thus have little effect on the total capacitance resulting in a low overall sensitivity of the sensor.

Figure 1:
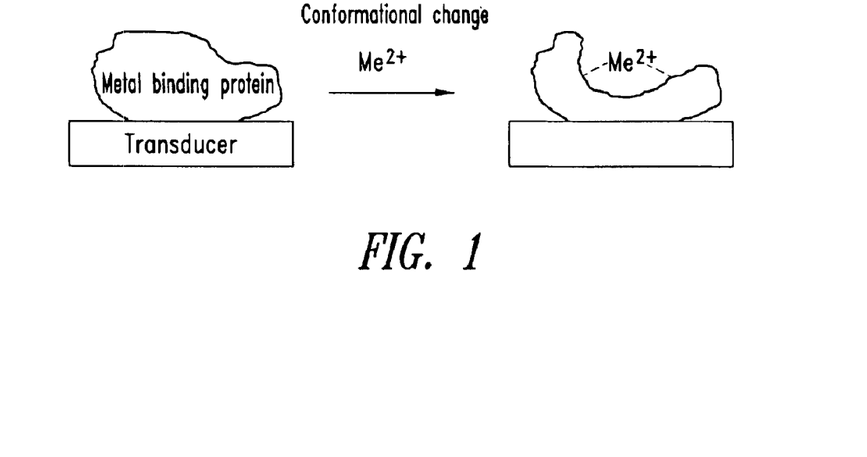
FIG. 1 shows schematically how a heavy metal specific protein is immobilized on the metal surface and how its three-dimensional conformation is changed when heavy metal ions bind to the protein.
Figure 2:
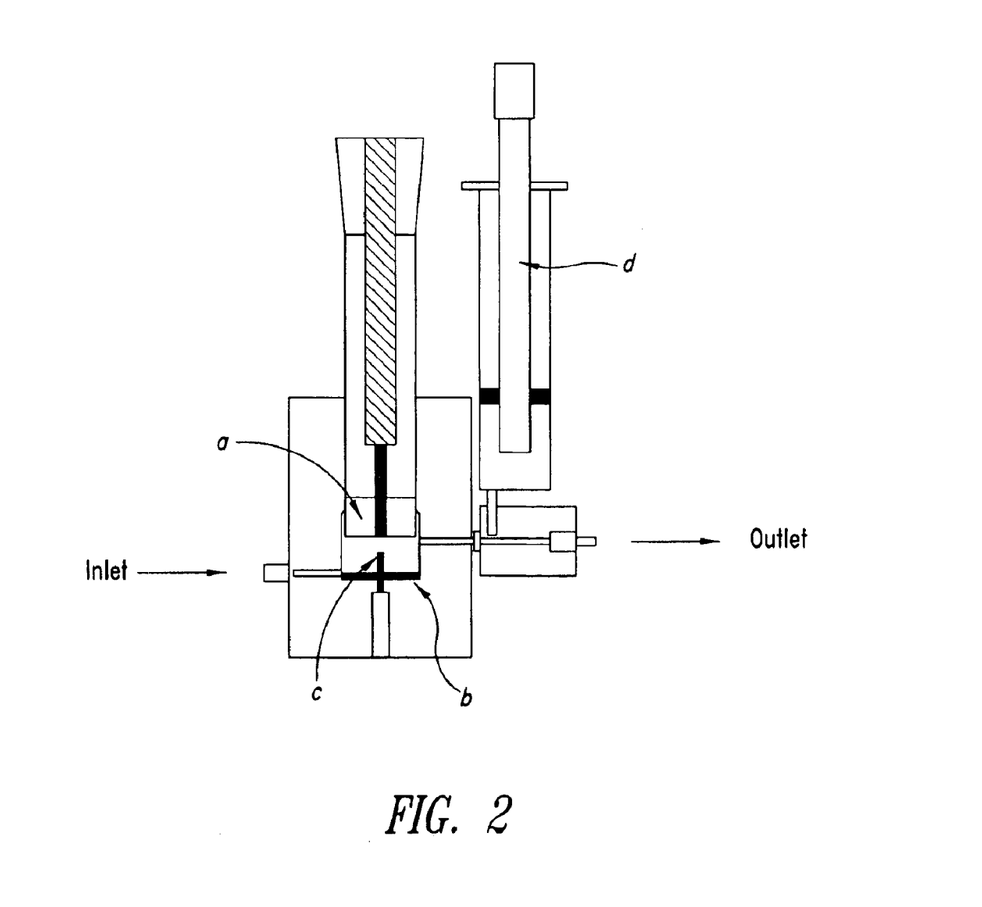
FIG. 2 shows the measuring flow cell, a) measuring electrode, b) auxiliary platinum foil electrode, c) platinum wire reference electrode, d) Ag/AgCl reference electrode.

The electrode is inserted into a cell which may be either of the cuvette type or a flow cell as shown in FIG. 2. The cell must contain an auxiliary electrode, typically a platinum foil which should be placed symmetrically and opposite to the measuring electrode. A reference electrode, typically SCE or Ag/AgCl, is placed in the cell so that the voltage drop between the reference and measuring electrodes due to capacitive or Faradaic currents becomes very small. In some cases the performance may be improved if a very small additional reference electrode is used, see FIG. 1c and the SCE reference is moved away, FIG. 1d. A flow cell gives more precise control over the mass transfer to the measuring electrode and injection of sample and cleaning up is more easily automated. Flow cells with volumes of 2 ml and 10 µl were found to have about the same sensitivity. A flow cell with disposable electrodes made by sputtering gold on silicon also had similar properties.

The electrodes are connected to a fast potentiostat which in turn is controlled by a microprocessor. The potentiostat will keep the measuring electrode at a pre-set value versus the reference electrode. A potentiostatic perturbation is imposed on the measuring electrode. It may be a sinusoidal wave, it may be a step voltage or any other wave-form which enables interpretation of the results. The currents caused by the perturbation voltage are used for evaluation of the capacitance of the measuring electrode. It can be done for sinusoidal perturbations by separating the in-phase and out-phase part of the current in a lock-in amplifier. If this is repeated at different frequencies an impedance spectra can be obtained. In all cases the capacitance can be evaluated from the current responses. As usual in electrochemistry the role of current and potential can be reversed, i.e. a galvanostatic step in current will cause the potential to change. This change can be used for evaluation of the capacitance, although using different algorithms.

A known volume of sample is normally mixed with a known volume of a conducting liquid in e.g. a cuvette in a batch type cell. For a flow cell, a known volume is injected into a conducting carrier flow pumped with a distinct flow rate. The conducting liquids are normally buffers with ionic strengths from a few millimolar and up. The sample can be in a non-conducting medium but a conducting solution must fill the cell when measurements are made.

The present invention will now be further described with reference to the following examples. The examples are given for the purpose of information and are not intended to limit the scope of the present invention.

EXAMPLE 1

The fusion proteins GST-SmtA and MerR were produced as described below and dissolved in phosphate buffered saline (70 mM NaCl, 1.3 mM KCl, 5 mM $Na_2HPO_4$, 0.9 mM $KH_2PO_4$, pH 7.3) containing 50% (v/v) glycerol to a final concentration of 1 mg/ml protein. Thioctic acid and glutaraldehyde were purchased from Sigma and 1-(3-dimethylaminopropyl)-3-ethyl-carbodiimide hydrochloride was obtained from Fluka. 1-dodecanethiol and the gold rods used for the electrodes (Cat. No 26,583-7, =3 mm) came from Aldrich Chemicals. The heavy metals $CuCl_2*2H_2O$, $ZnCl_2$, $HgCl_2$ and $Cd(NO_3)_2*4H_2O$ were all from Merck (Darmstadt, Germany). PEGDGE was achieved from Polysciences Inc. (USA). All other reagents used were of analytical grade.

The biosensors were prepared by immobilizing fusion proteins on the gold surface by EDC-mediated coupling, PEGDGE entrapment or glutaraldehyde coupling. In all cases 20 μl of the dissolved fusion proteins were diluted with 480 μl 100 mM borate buffer, pH 8.75 and the solution was ultrafiltered on a micro-filter (Amicon, USA) with a molecular cut-off of 3000 D. After the ultrafiltration the filter was turned over to recover fusion protein and its concentration was adjusted to 0.04 mg/ml in borate buffer. Gold electrodes were cleaned and pretreated with self-assembling of thioctic acid, as described earlier by Berggren and Johansson [Berggren, C., Johansson, G., Anal. Chem., Submitted ]. As the MerR protein is sensitive against oxidation in air, the preparation of these electrodes was performed under nitrogen atmosphere.

EDC-mediated Coupling:

The self-assembled electrodes were thoroughly washed with ethanol, dried and thereafter activated in a 1% solution of 1-(3-dimethylaminopropyl)-3-ethyl-carbodiimide hydrochloride in dried acetonitrile for 5 hours. After washing with 100 mM borate buffer, pH 8.75 the electrodes were dipped into the protein solution at a temperature of 4° C. for 24 hours. Subsequently each electrode was thoroughly washed with borate buffer and dipped into a solution of 1-dodecanethiol for 20 minutes.

PEGDGE entrapment:

The thioctic acid activated electrode was covered with 1.5 μl of a 0.04 mg/ml protein solution in 100 mM borate buffer containing 30% (w/w) PEGDGE and the electrode was incubated at 45° C. for 15 minutes. Afterwards the electrode was treated with 1-dodecanethiol for 20 minutes, washed with borate buffer and placed in the measuring cell.

Glutaraldehyde Coupling:

Prior to glutaraldehyde immobilization the electrode was modified with cysteamine, instead of thioctic acid. The dried electrode was dipped into a solution containing 12.5% (w/v) glutaraldehyde in coupling buffer (0.1 M sodium phosphate, 0.15 M NaCl, pH 7) and 6 g/l $NaCNBH_3$ for 4 hours. Then, the electrode was washed thoroughly with coupling buffer and dipped into the protein solution (0.04 mg/ml) with 6 g/l $NaCNBH_3$ for 4 hours.

Finally the electrode was washed thoroughly with coupling buffer before use.

Capacitance Measurements:

The biosensor was arranged as the working electrode in a three-electrode system connected to a fast potentiostat, as shown in FIG. 1. It was placed in a flow cell with a dead volume of 10 μl which was built in house. A platinum foil served as the auxiliary and a platinum wire as the reference electrode. An extra reference electrode (Ag/AgCl) was placed in the outlet stream, as the platinum does not have a defined potential. The buffer solution was pumped by a peristaltic pump with a flow rate of 0.5 ml/min. through the flow cell. Samples were injected into the flow via a 250μl sample loop. The buffer used was 10 MM borate, pH 8.75. Before use it was filtered through a 0.22 μm millipore filter and degassed.

The working electrode had a rest potential of 0 mV vs. the Ag/AgCl reference electrode. When measuring, a potential step of 50 mV was applied and the current transient that followed when the potential increased was assumed to follow the equation:

$$i(t)=u/R_s\exp(-t/R_s \cdot C_1) \qquad (1)$$

where i(t) is the current at time t, u is the amplitude of the potential pulse applied, R is the resistance between the gold electrode and the reference electrode, $C_1$ is the total capacitance over the immobilized layer and t is the time elapsed after the potential pulse was applied. The current values were collected with a frequency of 50 kHz and the first ten values were used in the evaluation of the capacitance. Each capacitance value was calculated as the mean of ten measurements.

With capacitance measurements the interface between a conducting electrode and the sample solution is studied. This interface is called the electrical double-layer as charges and dipoles will orient with opposite signs on the conducting surface and in the solution. When the heavy metal specific protein is immobilized on the electrode surface it will exchange the buffer solution at the surface and a charge separation will take place, leading to a decrease in capacitance. The detection principle used in this work is based on monitoring a conformational change resulting from a specific binding of a certain heavy metal ion to an immobilized protein on the electrode surface (see FIG. 2). As the sensor measures changes in conformation, it is important to optimize the immobilization conditions.

Figure 3:
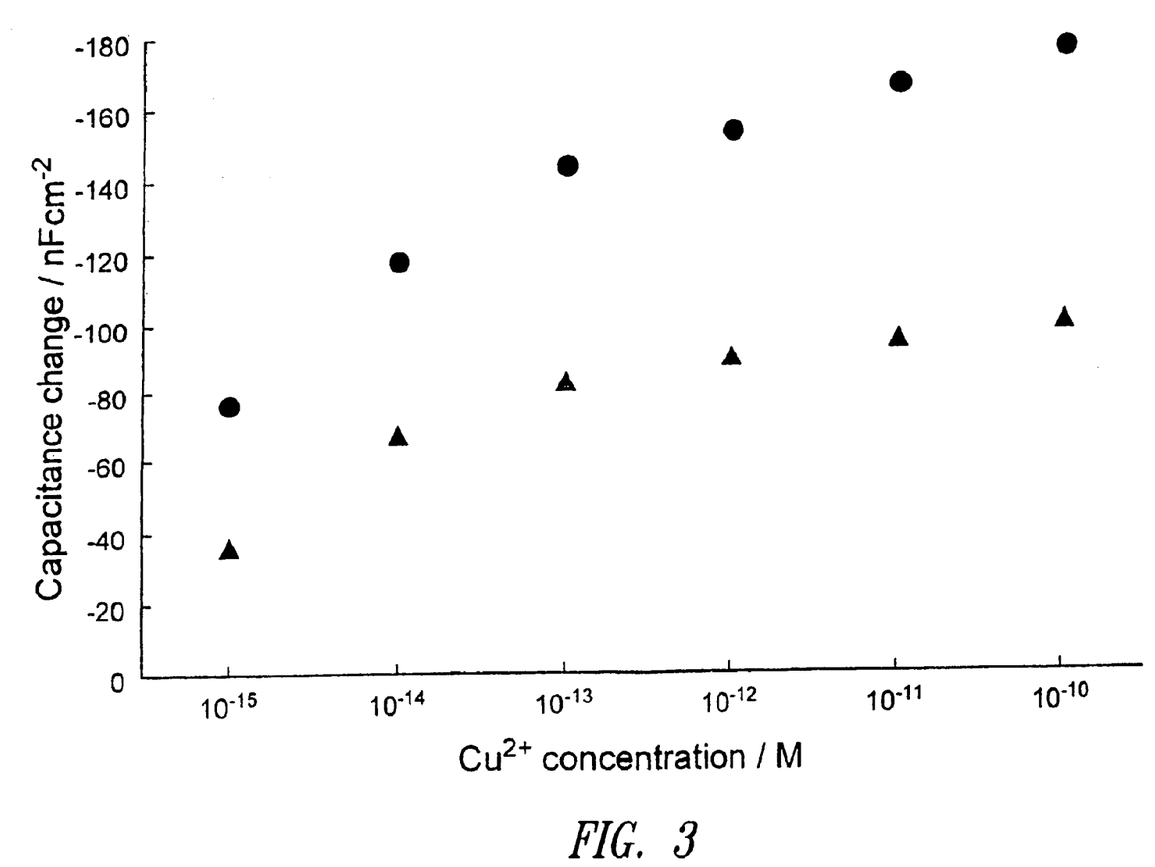
FIG. 3 shows the response for copper for electrodes immobilized with GST-SmtA protein with EDC-mediated coupling (upper curve) and PEGDGE entrapment (lower curve). See example 1 for more details.

Immobilization of the Recognition Element:

A gold electrode was used as conducting noble metal surface in this work. To immobilize the recognition elements, which were different fusion proteins, the gold surface had to be modified in some way. A well-known and easy method is to use self-assembling of thiol-, sulphide- or disulphide compounds onto the gold surface. Self-assembling is a spontaneous process producing well-ordered monolayers of molecules. Furthermore the binding between sulphur and gold is rather strong, an important stability aspect in biosensor design, where leaking off of the recognition element results in loss of activity. Three different immobilization methods were studied in order to produce an optimal surface for capacitance measurements, namely; EDC-mediated coupling, PEGDGE entrapment and glutaraldehyde coupling. In all cases a short compound containing one or more sulphur groups was first self-assembled on the gold surface. The EDC-mediated coupling is producing a monolayer of protein molecules on the surface without any crosslinking between individual molecules. This method has previously been shown to be successful for immobilization of antibodies onto gold electrodes with self-assembled thioctic acid on the surface [Duan, C.; Meyerhoff, M. E., Anal. Chem., 66, 1994, 1369–1377]. With PEGDGE immobilization the protein will be entrapped in a polymer network, where the heavy metals can diffuse into the pores of the polymer. Calibration curves for copper are shown in FIG. 3 for EDC coupling (upper curve) and for PEGDGE entrapment (lower curve) of the protein. It was found that the sensitivity was much higher for the EDC activated electrode. A possible explanation might be that the PEGDGE entrapment prohibits the conformational change of the fusion protein to some extent. The reproducibility was also lower for the PEGDGE electrodes, because of the difficulty to deposit exactly the same amount of the protein/crosslinker for each electrode. Further experiments will be performed with less concentration of PEGDGE to decrease the crosslinking and thereby produce a less rigid protein layer. Glutaraldehyde is also a crosslinker, but in this case the surface was first activated by glutaraldehyde before the protein was added. Also in this case it is very important to optimize the amount of crosslinker in order not to crosslink the protein too much, making it rigid and not susceptible to conformational changes. All further experiments were performed with electrodes manufactured by the EDC method.

EXAMPLE 2

Cyclic voltammograms were recorded in 5 mM $K_3[Fe(CN)_6]$, 1 M KCl in a batch cell, with the unmodified/modified gold electrode as working electrode a SCE as reference and a platinum flag as auxiliary electrode. The scan rate was 50 mV/s. The electrodes were connected to a Princeton Applied 274 A potentiostat, connected to a computer.

Figure 4:
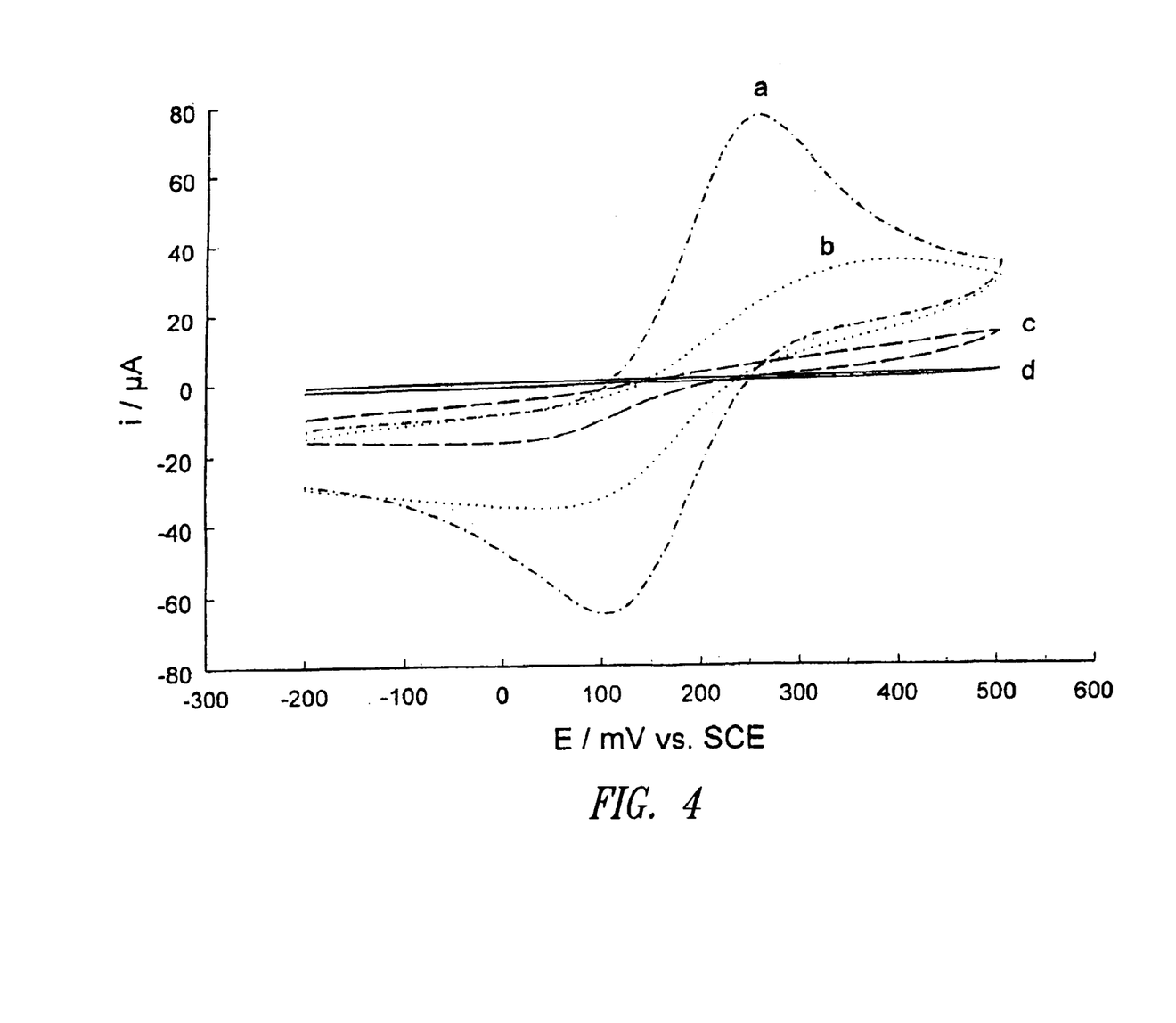
FIG. 4 shows the cyclic voltammetry responses recorded in a $Fe(CN)_6^{3-}$ solution when the measuring electrode was a) unmodified gold, b) gold modified with thioctic acid, c) as in b with additional modification with immobilized fusion protein GST-SmtA and d) as in c with additional modification with 1-dodecanethiol. More details are given in example 2.

In order to develop a sensitive affinity sensor based on capacitance measurements the immobilization layer has to be as thin as possible and well-ordered. Defect sites in the monolayer might lead to penetration of solution molecules through the layer and close to the metal surface, leading to short-circuiting of the recognition layer with highly conducting aqueous channels. The result will be that capacitance changes will be smaller or absent for such defect sensors. The importance of good insulation of the electrode surface has earlier been demonstrated [Berggren, C.; Johansson, G. *Anal. Chem.* Submitted]. The degree of insulation can be studied by having a small permeable redox couple in solution. In FIG. 4 it is shown how the blocking increases for each additional layer. For a clean gold surface the redox couple $K_3[Fe(CN)_6]$ is oxidized and reduced at the metal surface. A surface covered with self-assembled thioctic acid reduces the access to the surface. Immobilization of the protein further insulates the surface, but it is not until the treatment in 1-dodecanethiol that the oxidation/reduction peaks totally disappears. All electrodes in the following experiments were therefore treated twenty minutes with 1-dodecanethiol.

EXAMPLE 3

Figure 5:
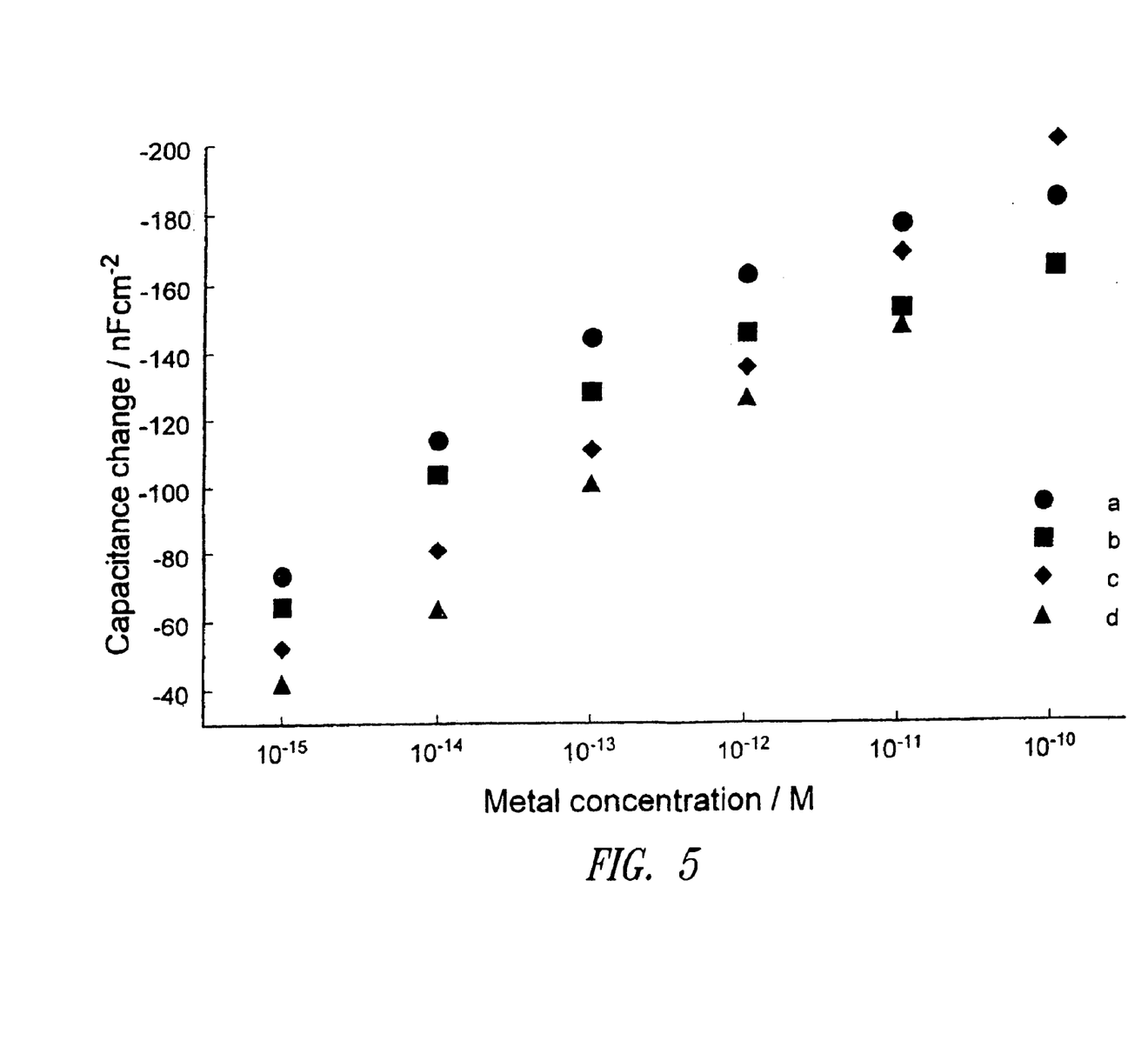
FIG. 5 shows capacitance change versus heavy metal ion concentration for a GST-SmtA immobilized electrode. Curve 1) shows the response for $Zn^{2+}$, curve 2) for $Hg^{2+}$, curve 3) for $Cd^{2+}$ and curve 4) for $Cu^{2+}$. The measurements were performed in 100 mM borate buffer, pH 8.75 at a flow rate of 0.5 ml/min. Samples with a volume of 250 µl were injected. For more details see example 3.
Figure 6:
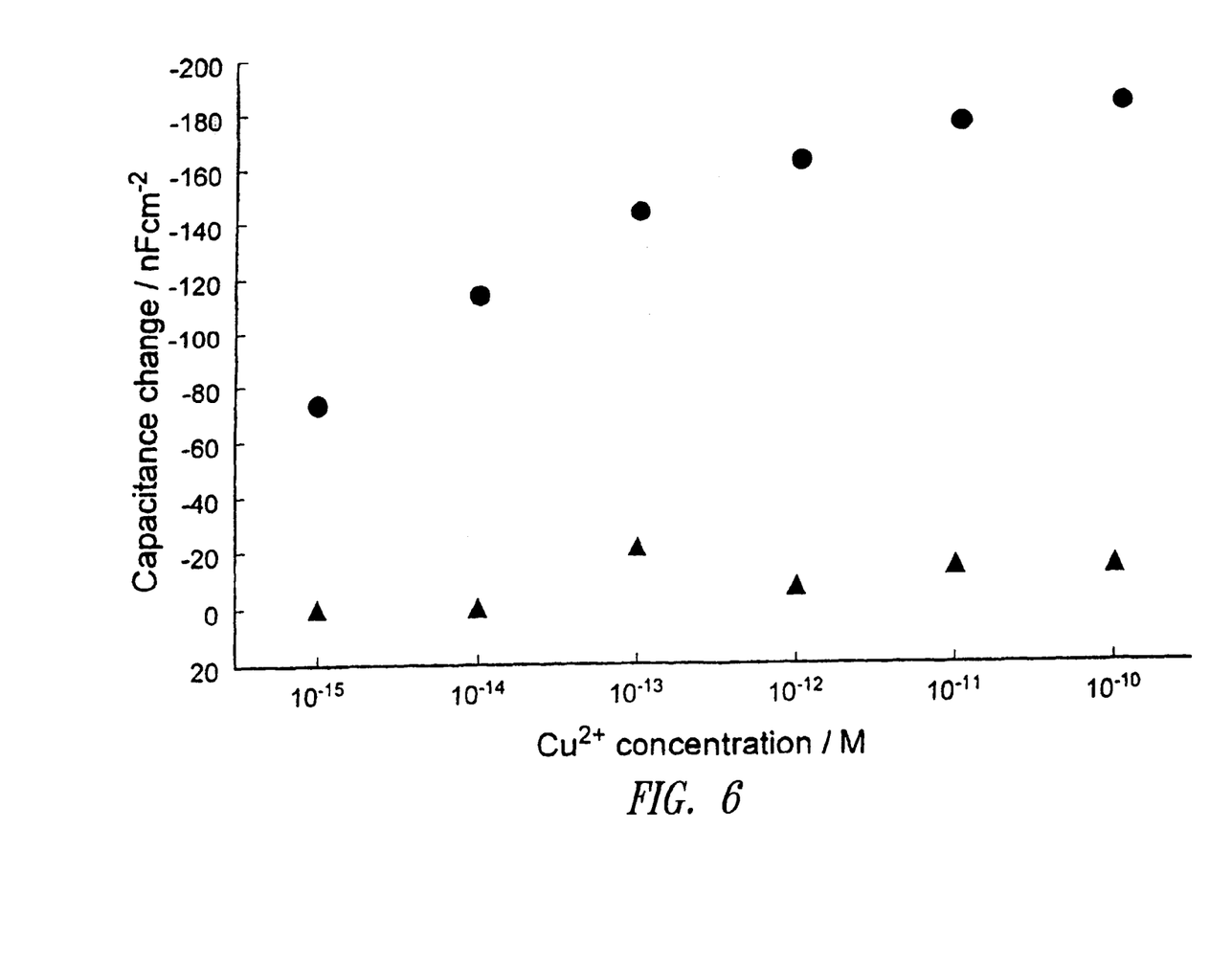
FIG. 6 shows capacitance change versus $Cu^{2+}$ concentration for electrodes using EDC coupling of protein. Upper curve shows the signal for the GST-SmtA-based electrode and the lower curve represents the signal recorded by a blank electrode with BSA on the surface. The measurements were performed in 100 mM borate buffer, pH 8.75 at a flow rate of 0.5 ml/min. Samples with a volume of 250 µl were injected. More details are given in example 3.

Characteristics such as sensitivity, selectivity, response time, stability and electrode surface regeneration possibility were studied in this work. However, the GST-SmtA based electrodes were more thoroughly studied, but some characteristics were studied for MerR protein based electrodes as well, and obtained results were evaluated and compared. The affinity of the GST-SmtA protein was studied for copper, cadmium, mercury and zinc (see FIG. 5). The electrodes responded for all four metal ions with decreasing sensitivity for Cu>Cd>Hg>Zn, well in agreement with previously reported results obtained with solution of this engineered protein [Shi, J.; Lindsay, W. P.; Huckle, J. W.; Morby, A. P.; Robinson, N. J. *FEBS*, 303, 1992 159–163]. The detection limit was in the femtomolar molar range or below for each of the studied heavy metals. Reference electrodes, equally prepared but using BSA instead of GST-SmtA resulted in hardly detectable signals for Cu and no signals at all for the other ions (see FIG. 6). Similar results were obtained when using another protein, urease, well known to bind heavy metals. For the latter case, the absence of any detectable signals was assumed to be due to lack of conformational changes upon exposure to heavy metal.

Figure 7:
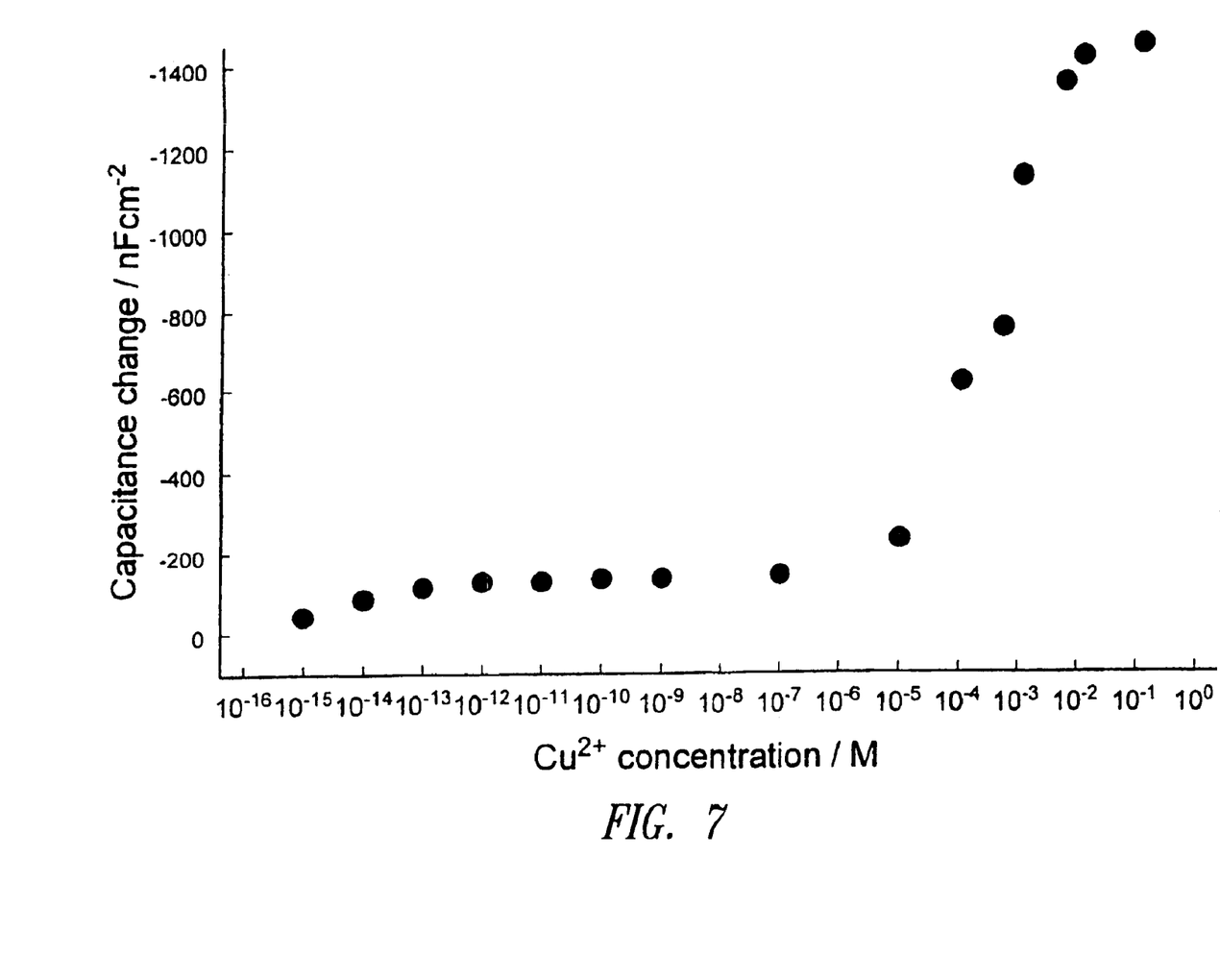
FIG. 7 shows capacitance change versus $Cu^{2+}$ concentration in the range $10^{-15}$ M to 0.1 M. The measurements were performed in 100 mM borate buffer, pH 8.75 and a flow rate of 0.5 ml/min. Samples with a volume of 250 µl were injected. For details see example 3.
Figure 8:
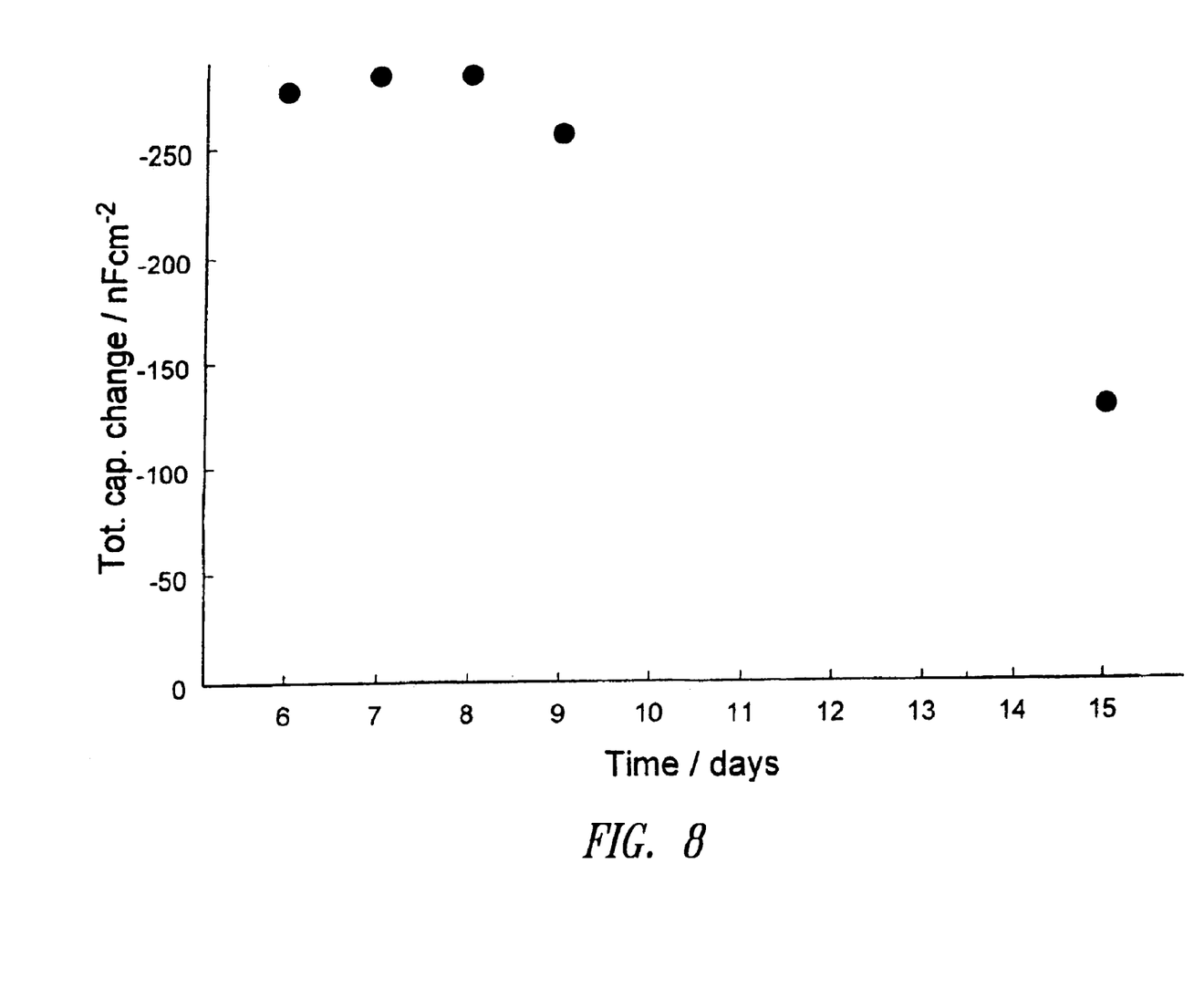
FIG. 8 shows a stability study for a GST-SmtA electrode according to the present invention. A calibration curve from 1 femtomolar to 100 picomolar was recorded each day and the total capacitance change vs. time was plotted. Between measurements the sensor was stored at 4° C. in 100 mM borate buffer pH 8.75. Details are given in example 3.

The activity of an GST-SmtA electrode was studied for an extended interval, Copper samples of concentrations of $10^{-15}$M to 0.1 M were injected and the capacitance changes were determined. A slow increase of the signal was obtained to approximately $10^{-5}$M thereafter the signal increase became much faster to approximately $10^{-2}$M, where saturation occurred (see FIG. 7). It is believed that the increase in the first part of the curve is due to the specific binding of heavy metal and that the second one probably is due to denaturation of the protein on the electrode surface. Inability to regenerate the electrode after injection of a 1 mM copper might support this assumption. The stability of the GST-SmtA based biosensor was studied for 16 days. A calibration curve between $10^{-15}$M to $10^{-10}$M Cu was measured each day and the total capacitance change vs. time is plotted in FIG. 8. Between measurements the sensor was stored at 4° C. in 100 mM borate buffer, pH 8.75. A loss of activity was observed after 10 days and it decreased with approximately 40% after 16 days.

The surface of the biosensor could be regenerated by injecting 250T1, 1 mM EDTA. It was found that if EDTA was injected just before storage the biosensor lost activity over night, but if the electrode was stored with heavy metal and the regeneration procedure took place immediately before measuring the next day no activity loss could be observed. The observed phenomenon was attributed to the assumption that the protein has a more open structure when the heavy metal ion is absent and hence this structure is more easily denatured. Regeneration with EDTA after injection of a sample containing as much as 1 mM $Cu^{2+}$ was unsuccessful, attributed to irreversible surface denaturation by this high metal ion concentration.

EXAMPLE 4

Figure 9:
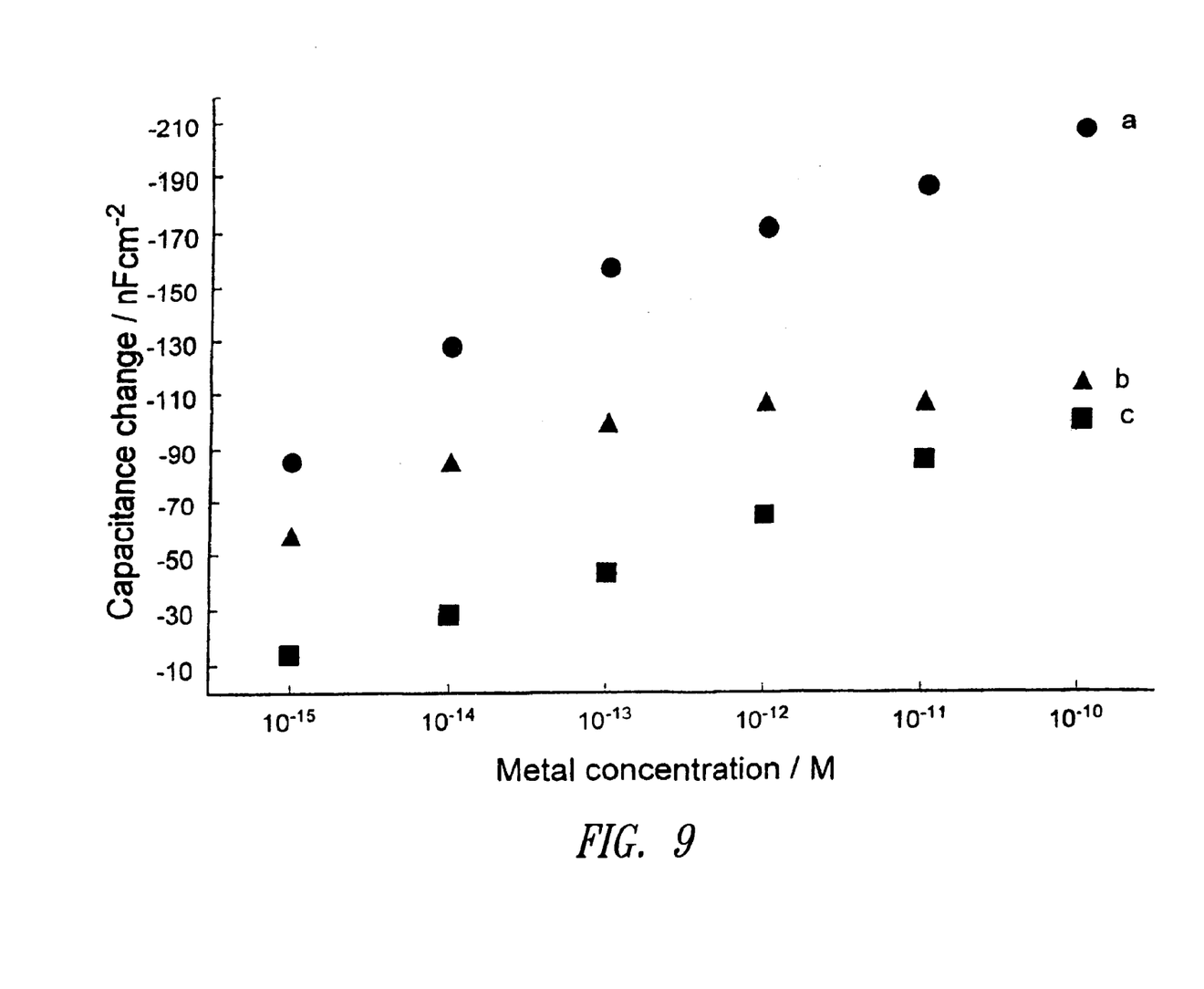
FIG. 9 shows capacitance change versus heavy metal ion concentration for a MerR immobilized electrode. Curve 1) shows the response for $Cd^{2+}$, curve 2) for $Cu^{2+}$ and curve 3) for $Hg^{2+}$. The measurements were performed in 100 mM borate buffer, pH 8.75 and a flow rate of 0.5 ml/mm. Samples with a volume of 250 µl were injected. More details are given in example 4.

Biosensors were constructed using the second engineered protein, MerR, and signals were recorded for Cu, Cd, Hg and Zn. This protein was reported to be highly specific towards mercury (II) ions [Frantz, B.; O'Hallaran, T. V.; *Biochemistry*, 29, 1990 4747–4751]. The protein was immobilized onto the gold surface only by using the EDC-coupling method. Obtained results were in good agreement with reported properties, the MerR-based electrodes displayed highest selectivity for mercury and that this electrode showed higher selectivity than the GST-SmtA based electrodes (see FIG. 9).

Listing of claims:

1. A method for producing a metal ion-specific capacity affinity sensor suitable for determining the presence of a certain heavy metal ion of interest in a contacting solution by capacitance measurement, comprising the steps of:
   a) providing a piece of a noble metal having a surface;
   b) providing a first self-assembling monolayer-forming molecule comprising a coupling group;
   c) contacting said noble metal piece in step a) with the first self-assembling monolayer-forming molecule in step b), thereby obtaining a first self-assembling monolayer on said surface of said noble metal piece;
   d) contacting said first self-assembling monolayer on said noble metal piece with a molecule specifically binding said heavy metal ion, thereby coupling said molecule to said first self-assembling monolayer; and
   e) contacting the piece obtained in step d) with a second self-assembling monolayer-forming molecule, thereby obtaining a noble metal surface that is at least 90% covered with a self-assembling monolayer,
   wherein the coupling reaction in step d) is carried out in presence of polyethylene-glycol-diglycidyl-ether such that the polyethylene-glycol-diglycidyl-ether entraps the molecule and facilitates the coupling of said molecule to the first self assembling monolayer.

2. A method according to claim 1, characterized in that said second self-assembling monolayer-forming molecule is a thiol comprising 3–25 carbon atoms in a straight saturated chain.

3. A method according to claim 2, wherein said second self-assembling monolayer-forming molecule is 1-dodecanethiol.

4. A method according to claim 1, wherein said piece of a noble metal in step a) is a rod.

5. A method according to claim 1, wherein said piece of a noble metal in step a) is a piece of insulating material on which a noble metal is sputtered or printed.

6. A method according to claim 5, wherein said piece of insulating material is comprised of a substance selected from the group consisting of glass, silicon, and quartz.

7. A method according to claim 1, wherein the noble metal surface obtained in step e) is at least 95% covered with a self-assembling monolayer.

8. A method according to claim 1, wherein the noble metal surface obtained in step e) is at least 97% covered with a self-assembling monolayer.

9. A method according to claim 1, wherein the noble metal surface obtained in step e) is at least 99% covered with a self-assembling monolayer.

10. A metal ion-specific capacity affinity sensor comprising a piece of a noble metal having a surface to which molecules specifically binding a certain heavy metal ion of interest have been bound, characterized in that said molecules specifically binding to said heavy metal ion are coupled to a self-assembling monolayer covering at least 90% of said surface of said noble metal piece, and characterized in that said sensor has been produced by a method according to claim 1 or claim 2.

11. A sensor according to claim 10, characterized in that said molecules specifically binding to said heavy metal ion are selected from the group of proteins consisting of SEQ.ID.NO.1, SEQ.ID.NO.2, SEQ.ID.NO.3, SEQ.ID.NO.4, and functional derivatives thereof, wherein the functional derivatives have binding characteristics equivalent to SEQ.ID.NO.1, SEQ.ID.NO.2, SEQ.ID.NO.3, or SEQ.ID.NO.4.

12. A sensor according to claim 10, wherein said piece of a noble metal is a rod.

13. A sensor according to claim 10, wherein said piece of a noble metal is a piece of insulating material on which a noble metal is sputtered.

14. A sensor according to claim 13, wherein said piece of insulating material is comprised of a substance selected from the group consisting of glass, silicon, and quartz.

15. A sensor according to claim 10, wherein said surface of said noble metal piece is at least 95% covered with a self-assembling monolayer.

16. A sensor according to claim 10, wherein said surface of said noble metal piece is at least 97% covered with a self-assembling monolayer.

17. A sensor according to claim 10, wherein said surface of said noble metal piece is at least 99% covered with a self-assembling monolayer.

18. A method for qualitatively determining the presence of a certain heavy metal ion of interest in a liquid sample, comprising the steps of:
   a) providing a sensor according to claim 10;
   b) contacting said sensor with a reference liquid not containing said heavy metal ion of interest and determining the capacitance;
   c) contacting said sensor with a liquid sample suspected of containing said heavy metal ion of interest and determining the capacitance; and
   d) calculating the difference between the capacitance of the liquid sample and the capacitance of the reference liquid.

19. A method according to claim 18, wherein said heavy metal ion of interest is selected from the group consisting of $Zn^{2+}$, $Hg^{2+}$, $Cd^{2+}$, $Cu^{2+}$, and $Pb^{2+}$.

20. A method for quantitatively determining the presence of a certain heavy metal ion of interest in a liquid sample, comprising the steps of:
   a) providing a sensor according to claim 10;
   b) contacting said sensor with a reference liquid not containing said heavy metal ion of interest and determining the capacitance;
   c) contacting said sensor with a liquid sample suspected of containing said heavy metal ion of interest and determining the capacitance;
   d) calculating the difference between the capacitance of the liquid sample and the capacitance of the reference liquid; and
   e) calculating the amount of said heavy metal ion of interest using prerecorded calibration data.

* * * * *

UNITED STATES PATENT AND TRADEMARK OFFICE
CERTIFICATE OF CORRECTION

PATENT NO.    : 6,933,153 B1
DATED         : August 23, 2005
INVENTOR(S)   : Mattiasson et al.

It is certified that error appears in the above-identified patent and that said Letters Patent is hereby corrected as shown below:

<u>Title page,</u>
Item [56], References Cited, OTHER PUBLICATIONS, "Berggren, C. et al, Analytical Chemistry 1997, 69, 3651-1657" should read as -- Berggren, C. et al, Analytical Chemistry 1997, 69, 3651-3657 --.

Signed and Sealed this

Fifteenth Day of November, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 289
<212> TYPE: PRT
<213> ORGANISM: Synechococcus sp.

-continued

```
<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
    210                 215                 220

Arg Gly Ile Pro Met Thr Ser Thr Thr Leu Val Lys Cys Ala Cys Glu
225                 230                 235                 240

Pro Cys Leu Cys Asn Val Asp Pro Ser Lys Ala Ile Asp Arg Asn Gly
                245                 250                 255

Leu Tyr Tyr Cys Ser Glu Ala Cys Ala Asp Gly His Thr Gly Gly Ser
            260                 265                 270

Lys Gly Cys Gly His Thr Gly Cys Asn Cys Ser Glu Phe Ile Val Thr
        275                 280                 285

Asp

<210> SEQ ID NO 2
<211> LENGTH: 144
<212> TYPE: PRT
<213> ORGANISM: Pseudomonas aeruginosa

<400> SEQUENCE: 2

Met Glu Asn Asn Leu Glu Asn Leu Thr Ile Gly Val Phe Ala Lys Ala
1               5                   10                  15

Ala Gly Val Asn Val Glu Thr Ile Arg Phe Tyr Gln Arg Lys Gly Leu
            20                  25                  30

Leu Leu Glu Pro Asp Lys Pro Tyr Gly Ser Ile Arg Arg Tyr Gly Glu
        35                  40                  45

Ala Asp Val Thr Arg Val Arg Phe Val Lys Ser Ala Gln Arg Leu Gly
    50                  55                  60
```

```
Phe Ser Leu Asp Glu Ile Ala Glu Leu Leu Arg Leu Glu Asp Gly Thr
 65                  70                  75                  80

His Cys Glu Glu Ala Ser Ser Leu Ala Glu His Lys Leu Lys Asp Val
                 85                  90                  95

Arg Glu Lys Met Ala Asp Leu Ala Arg Met Glu Ala Val Leu Ser Glu
            100                 105                 110

Leu Val Cys Ala Cys His Ala Arg Arg Gly Asn Val Ser Cys Pro Leu
            115                 120                 125

Ile Ala Ser Leu Gln Gly Gly Ala Ser Leu Ala Gly Ser Ala Met Pro
        130                 135                 140
```

<210> SEQ ID NO 3
<211> LENGTH: 145
<212> TYPE: PRT
<213> ORGANISM: Alcaligenes eutrophus

<400> SEQUENCE: 3

```
Met Asn Ile Gln Ile Gly Glu Leu Ala Lys Arg Thr Ala Cys Pro Val
  1               5                  10                  15

Val Thr Ile Arg Phe Tyr Glu Gln Glu Gly Leu Leu Pro Pro Pro Gly
             20                  25                  30

Arg Ser Arg Gly Asn Phe Arg Leu Tyr Gly Glu Glu His Val Glu Arg
         35                  40                  45

Leu Gln Phe Ile Arg His Cys Arg Ser Leu Asp Met Pro Leu Ser Asp
     50                  55                  60

Val Arg Thr Leu Leu Ser Tyr Arg Lys Arg Pro Asp Gln Asp Cys Gly
 65                  70                  75                  80

Glu Val Asn Met Leu Leu Asp Glu His Ile Arg Gln Val Glu Ser Arg
                 85                  90                  95

Ile Gly Ala Leu Leu Glu Leu Lys His His Leu Val Glu Leu Arg Glu
            100                 105                 110

Ala Cys Ser Gly Ala Arg Pro Ala Gln Ser Cys Gly Ile Leu Gln Gly
            115                 120                 125

Leu Ser Asp Cys Val Cys Asp Thr Arg Gly Thr Thr Ala His Pro Ser
        130                 135                 140

Asp
145
```

<210> SEQ ID NO 4
<211> LENGTH: 72
<212> TYPE: PRT
<213> ORGANISM: Pseudomonas aeruginosa

<400> SEQUENCE: 4

```
Ala Thr Gln Thr Val Thr Leu Ser Val Pro Gly Met Thr Cys Ser Ala
  1               5                  10                  15

Cys Pro Ile Thr Val Lys Lys Ala Ile Ser Glu Val Glu Gly Val Ser
             20                  25                  30

Lys Val Asp Val Thr Phe Glu Thr Arg Gln Ala Val Val Thr Phe Asp
         35                  40                  45

Asp Ala Lys Thr Ser Val Gln Lys Leu Thr Lys Ala Thr Ala Asp Ala
     50                  55                  60

Gly Tyr Pro Ser Ser Val Lys Gln
 65                  70
```